US00PP18094P2

(12) United States Plant Patent
Pieters

(10) Patent No.: US PP18,094 P2
(45) Date of Patent: Sep. 25, 2007

(54) *CHRYSANTHEMUM* PLANT NAMED 'PPP CON OR05'

(50) Latin Name: *Chrysanthemum morifolium*
Varietal Denomination: PPP CON OR05

(75) Inventor: Dirk Pieters, Oostnieuwkerke (BE)

(73) Assignee: Pieters Plant Production, Oostnieuwkerke (BE)

( * ) Notice: Subject to any disclaimer, the term of this patent is extended or adjusted under 35 U.S.C. 154(b) by 0 days.

(21) Appl. No.: 11/414,915

(22) Filed: Apr. 29, 2006

(51) Int. Cl.
*A01H 5/00* (2006.01)

(52) U.S. Cl. ..... Plt./290

(58) Field of Classification Search ..... Plt./290, Plt./293, 287
See application file for complete search history.

*Primary Examiner*—Kent Bell
*Assistant Examiner*—June Hwu

(57) ABSTRACT

A new and distinct *Chrysanthemum* plant cultivar is disclosed, characterized by large decorative type inflorescences, consistent flowering response to short days, blooming consistently after 49 days of short day length, bright orange ray florets, free branching habit, and a consistent natural season flowering habit during the second week of September.

1 Drawing Sheet

Latin name of the genus and species: *Chrysanthemum morifolium.*
Variety denomination: 'PPP CON OR05'.

BACKGROUND OF THE INVENTION

The new cultivar 'PPP CON OR05' is a product of a cross between the female parent 'Sapiro Red' (undistributed in the United States) and the male parent 'Dark Veria' (U.S. Plant Pat. No. 10,215). The new cultivar was discovered and selected by Dirk Pieters in September 2003 in Oostnieuwkerke, Belgium.

Asexual reproduction of the new cultivar 'PPP CON OR05' by terminal cuttings and tissue culture was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP CON OR05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP CON OR05.' These characteristics in combination distinguish 'PPP CON OR05' as a new and distinct *Chrysanthemum*-cultivar:

1. Large bright orange inflorescence;
2. Consistent flowering response to short days, blooming consistently after 49 days of short day length;
3. Free branching habit; and
4. Consistent natural season flowering habit during the second week of September.

Plants of the new cultivar 'PPP CON OR05' are similar to plants of the female parent variety, 'Sapiro Red,' in most horticultural characteristics, however, plants of the new cultivar 'PPP CON OR05' bloom earlier than the female parent. Also, the ray florets of 'PPP CON OR05' are dark orange compared to the dark red of the female parent. Finally, 'Sapiro Red' has a weaker vigor than the new cultivar 'PPP CON OR05.'

Plants of the new cultivar 'PPP CON OR05' are similar to plants of the male parent 'Dark Veria' in most horticultural characteristics, however, plants of the new cultivar 'PPP CON OR05' are taller and wider. Also, 'PPP CON OR05' has more inflorescences per lateral branch and bright orange ray florets compared to the yellow ray florets of the male parent. Finally, the new cultivar has more ray florets per inflorescence and a larger inflorescence diameter.

In comparison to the commercially available variety 'GEDI THREE PORA' (U.S. Plant Pat. No. 17,067) 'PPP CON OR05' is taller and has a wider plant spread. Additionally, the new variety 'PPP CON OR05' has more ray florets per inflorescence and has less inflorescence per lateral branch. Further, the ray florets of 'PPP CON OR05' are a brighter, more intense orange-red compared to the greyed-orange ray florets of the comparable variety 'GEDI THREE PORA.'

BRIEF DESCRIPTION OF THE PHOTOGRAPH

The accompanying photograph in FIG. 1 illustrates in full color a typical plant of 'PPP CON OR05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP CON OR05' plants grown in Oxnard, Ventura County, Calif., during the months of May through September 2005.

The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP CON OR05.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 33 cm.
Plant spread: Approximately 50 cm.
Growth rate: Moderate.
Branching characteristics: Free Branching.
Length of lateral branches: Approximately 29 cm.
Number of leaves per lateral branch: Approximately 18.
Age of plant described: Approximately 125 days.

FOLIAGE

Leaf:
*Arrangement.*—Alternate single.
*Average length.*—Approximately 4.5 cm.
*Average width.*—Approximately 3.5 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 1.5 cm.
*Color.*—Young foliage upper side: Near Green 137A. Young foliage under side: Near Green 137D. Mature foliage upper side: Near Yellow-Green 147A. Mature foliage under side: Near Green 137B.
*Venation.*—Type: Palmately net. Venation color upper side: Near Yellow-Green 147C. Venation color under side: Near Yellow-Green 147C.

Petiole:
*Average length.*—Approximately 1 cm.
*Color.*—Near Yellow-Green 147B.
*Diameter.*—Approximately 0.2 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately second week in September.
*Number of inflorescences per lateral branch.*—Approximately 15.
*Inflorescence diameter.*—Approximately 5.2 cm.
*Inflorescence depth.*—Approximately 1.9 cm.
*Inflorescence longevity on plant.*—Approximately 28–34 days.
*Persistence.*—Persistent.

Ray florets:
*Appearance.*—Matte.
*Texture.*—Smooth.
*Average number of ray florets per inflorescence.*—224.
*Shape.*—Oblanceolate.
*Aspect.*—Flat.
*Margin.*—Entire.
*Apex.*—Obtuse.
*Length.*—Approximately 2 cm.
*Width.*—Approximately 1.8 cm.
*Color.*—Upper surface at first opening: Near Red 46A. Upper surface at maturity: Near Orange-Red 34B. Upper surface at fading: Near Orange 26A. Under surface at first opening: Near Red 46A. Under surface at maturity: Near Orange-Red 31B. Under surface at fading: Near Orange 26C.

Disc florets:
*Appearance.*—Shiny.
*Texture.*—Smooth.
*Average number of florets per disc.*—Approximately 14.
*Shape.*—Cylindric.
*Apex.*—Obtuse.
*Average length.*—Approximately 0.3 cm.
*Average width.*—Approximately 0.1 cm.
*Color.*—At first opening: Near Yellow 9B. At maturity: Near Yellow 9A. At fading: Near Yellow-Orange 15B.

Peduncle:
*Length.*—At terminal end (shortest): Approximately 4 cm. At lateral end (longest): Approximately 11 cm.
*Angle to stem.*Acute.
*Strength.*—Moderate.
*Color.*—Near Green 139C.
*Habit.*—Upright.
*Diameter.*—Approximately 0.2 cm.
*Surface texture.*—Lightly pubescent.

Inflorescence bud:
*Length.*—Approximately 0.5 cm.
*Diameter.*—Approximately 0.8 cm.
*Form.*—Globular.
*Color.*—Near Green 139D.

Involucral bracts (phyllaries):
*Appearance.*—Matte.
*Texture.*—Lightly pubescent.
*Number.*—Approximately 25.
*Shape.*—Ovate.
*Margin.*—Entire.
*Apex.*—Acute.
*Length.*—Approximately 1 cm.
*Width.*—Approximately 0.2 cm.
*Color.*—Upper side: Near Green 137A. Under side: Near Green 137C.

REPRODUCTIVE ORGANS

Ray florets:
*Number of pistils per floret.*—1.
*Stigma shape.*—2 branched.
*Stigma color.*—Near Yellow 5A.
*Style color.*—Near Yellow-Green 154B.
*Style length.*—Approximately 0.5 cm.
*Stamens.*—Absent.

Disc florets:
*Number of pistils per floret.*—1.
*Stigma shape.*—Cylindric.
*Stigma color.*—Near Yellow 9A.

*Style length.*—Approximately 0.1 cm.
*Style color.*—Near Yellow 8C.
*Number of stamens per floret.*—Approximately 5.
*Anther shape.*—Tubular.
*Anther color.*—Near Yellow 9A.
*Pollen color.*—Near Yellow 9A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP CON OR05' as herein illustrated and described.

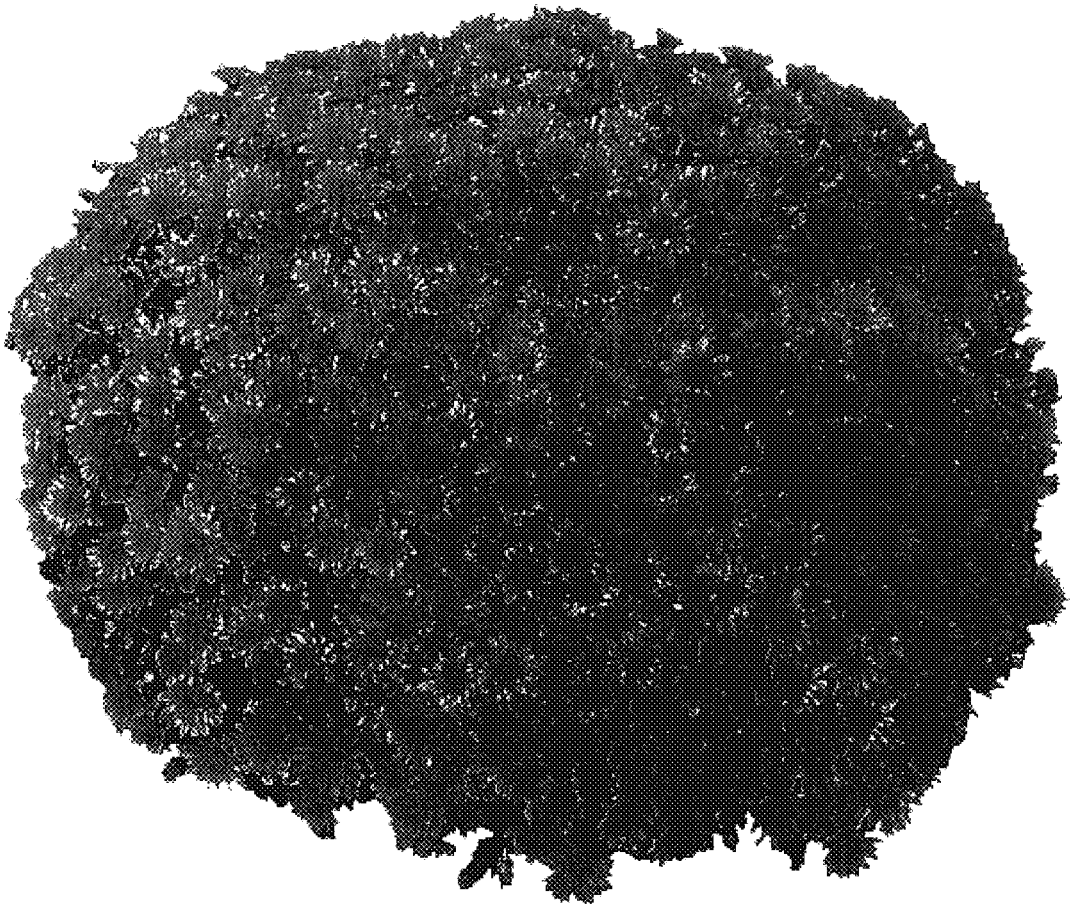

* * * * *